US010053459B2

(12) United States Patent
Mori et al.

(10) Patent No.: US 10,053,459 B2
(45) Date of Patent: Aug. 21, 2018

(54) LIFE-EXTENDING AGENT, LIFE EXTENSION METHOD USING THE LIFE-EXTENDING AGENT, NOVEL DUAL OXIDASE ACTIVATOR, METHOD FOR ACTIVATING DUAL OXIDASE, PRODUCTION OF LIFE-EXTENDING AGENT, AND PRODUCTION OF DUAL OXIDASE ACTIVATOR

(71) Applicants: National University Corporation Nagoya University, Nagoya-shi (JP); Mitsubishi Gas Chemical Company, Inc., Chiyoda-ku (JP)

(72) Inventors: Ikue Mori, Nagoya (JP); Hiroyuki Sasakura, Nagoya (JP); Kazuto Ikemoto, Niigata (JP); Masahiko Nakano, Niigata (JP)

(73) Assignees: National University Corporation Nagoya University, Nagoya-shi (JP); Mitsubishi Gas Chemical Company, Inc., Chiyoda-ku (JP)

( * ) Notice: Subject to any disclaimer, the term of this patent is extended or adjusted under 35 U.S.C. 154(b) by 0 days.

(21) Appl. No.: 15/512,895

(22) PCT Filed: Sep. 18, 2015

(86) PCT No.: PCT/JP2015/076796
§ 371 (c)(1),
(2) Date: Mar. 21, 2017

(87) PCT Pub. No.: WO2016/047637
PCT Pub. Date: Mar. 31, 2016

(65) Prior Publication Data
US 2017/0291898 A1    Oct. 12, 2017

(30) Foreign Application Priority Data

Sep. 22, 2014 (JP) ................................. 2014-193034

(51) Int. Cl.
*C07D 471/04* (2006.01)
*A61K 31/4745* (2006.01)

(52) U.S. Cl.
CPC ........ *C07D 471/04* (2013.01); *A61K 31/4745* (2013.01)

(58) Field of Classification Search
CPC .................................................. C07D 471/04
USPC ........................................................ 546/84
See application file for complete search history.

(56) References Cited

U.S. PATENT DOCUMENTS

| 8,946,423 B2 * | 2/2015 | Ikemoto | A61K 31/475 |
| | | | 546/84 |
| 2008/0279786 A1 | 11/2008 | Cash | |
| 2009/0148426 A1 | 6/2009 | Kishida et al. | |
| 2012/0116087 A1 * | 5/2012 | Edahiro | C07D 471/04 |
| | | | 546/84 |

FOREIGN PATENT DOCUMENTS

| EP | 1 588 709 A1 | 10/2005 |
| EP | 2 011 498 A1 | 1/2009 |
| JP | 6-128259 A | 5/1994 |
| JP | 2013-100323 A | 5/2013 |
| WO | 2007/034852 A1 | 3/2007 |
| WO | 2011/007633 A1 | 1/2011 |

OTHER PUBLICATIONS

International Search Report dated Dec. 22, 2015 in PCT/JP2015/076796 filed Sep. 18, 2015.
Harrison, David E. et al., "Rapamycin fed late in life extends lifespan in genetically heterogeneous mice," Nature, vol. 460, Jul. 16, 2009, 5 pages.
Martin-Montalvo, Alejandro et al., "Metformin improves healthspan and lifespan in mice," Nature Communications, Jul. 30, 2013, pp. 1-9.
Ishida, Toshimasa et al., "Formation of Imidazolopyrroloquinoline as Main PQQ Adduct with Amino Acid in Vitro: X-ray Structural Evidence," J. Am. Chem. Soc., vol. 117, No. 11, 1995, pp. 3278-3279.
Life Extension, PQQ Capsule with Bio PQQ, 10 mg, 30 Veggie Capsule [online], Mar. 12, 2012 [retrieval date Nov. 17, 2015, Internet:URL:http://jp.iherb.com/Life-Extension-PQQ-Caps-with-BioPQQ-10-mg-30-Veggie-Caps/25980, Shohin no Gaiyo, iHerb Customer Review, 4 pages.
Mukai, Kazuo et al., "Kangengata Pyrroloquinoline Quinone (PQQH2) no Ko Sanka Kassei no Hyoka," Vitamins, 2013, vol. 87, No. 4, 3 pages.
Naito, Yuji, "Ko Karei Iryo—Shindan to Chiryo no Saizensen Ko sanka Supplement no Erabikata," Modern Physician, Apr. 15, 2006, vol. 26, No. 4, pp. 547 to 550.
Supplement de Kenko wa Te ni Hairunoka PQQ(pyrroloquinoline Quinone) Kassei sanso Hogo Kino [online], Dec. 24, 2013, [retrieval date Oct. 27, 2015], Internet http://dietary-supplement.blog.jp/archives/3843119.html, Pyrroloquinoline Quinone no Supplement, 5 pages.

(Continued)

*Primary Examiner* — Taofiq A Solola
(74) *Attorney, Agent, or Firm* — Oblon, McClelland, Maier & Neustadt, L.L.P.

(57) ABSTRACT

The present invention provides a life-extending agent comprising pyrroloquinoline quinone and/or a derivative of the pyrroloquinoline quinone.

8 Claims, 2 Drawing Sheets

(56) References Cited

OTHER PUBLICATIONS

Q. Zhang, et al., "Pyrroioquinoline quinone rescues hippocampal neurons from glutamate-induced cell death through activation of Nrf2 and up-regulation of antioxidant gene", Genetics and Molecular Research, vol. 3. XP55440009, 2012, pp. 2652-2664.

Terry W. Snell, et al., "Antioxidants can extend lifespan of *Brachionus manjavacas* (Rotifera), but only in a few combinations", Biogerontology, vol. 13, No. 3, XP9502693, 2012, pp. 261-275.

Arthur Oubrie, "Structure and mechanism of soluble glucose dehydrogenase and other PQQ-dependent enzymes", Biochimica et Biophysica Acta (BBA), vol. 1647, No. 1-2, XP4417978, 2003, pp. 143-151.

Perry Marcone, "Generate Fresh Mitochondria with PQQ", Life Extension Magazine. XP55439811, 2011, pp. 1-6.

\* cited by examiner

LIFE-EXTENDING AGENT, LIFE EXTENSION METHOD USING THE LIFE-EXTENDING AGENT, NOVEL DUAL OXIDASE ACTIVATOR, METHOD FOR ACTIVATING DUAL OXIDASE, PRODUCTION OF LIFE-EXTENDING AGENT, AND PRODUCTION OF DUAL OXIDASE ACTIVATOR

TECHNICAL FIELD

The present invention relates to a novel life-extending agent, a life extension method using the life-extending agent, a novel dual oxidase activator, a method for activating dual oxidase, the production of a life-extending agent, and the production of a dual oxidase activator.

BACKGROUND ART

Although many attempts have been made for life extension, the possibility of scientific life extension has been found only recently.

Caloric restriction has heretofore been known as a method for causing life extension regardless of organism species. The caloric restriction prolongs average life and/or maximum life in a wide range of different organisms including yeasts, *Trochelminthes*, guppies, spiders, fruit-flies, hamsters, rats, and mice. In this context, the "caloric restriction" refers to the restriction of the total number of calories derived from carbohydrates, lipids, and/or proteins to a level that is 25% to 60% lower than the calories of freely fed control animals.

In addition, the caloric restriction also delays the development of aging-related diseases and thereby offers healthier life for a longer period, in addition to the prolonging of life. For example, the caloric restriction is known to delay the development of kidney diseases, autoimmune diseases, and diabetes mellitus in mammals.

Furthermore, the caloric restriction reduces even aging-related neuron loss in mouse models of Parkinson's disease and Alzheimer's disease. The caloric restriction has also been found to reduce a risk of cancer in mammals and to enhance DNA repair in the skin and other tissues after exposure to ultraviolet rays.

Such action of the caloric restriction on a wide range of organisms from unicellular organisms to very complicated organisms (including primates) is important from the viewpoint that the process of prolonging life is conserved across species. The rate of prolonging of life can reach 50% in rodents. However, calories necessary for organisms are usually at least 25% smaller than their consumed calories. Therefore, this prolonged life is obtained from considerable sacrifice such as hunger or limitation of activity (Patent Literature 1).

As another method, it is also possible to extend life by gene manipulation. However, the gene manipulation is not considered to be sufficiently safe and furthermore, cannot be readily applied.

Substances extending life have been found as a method for overcoming these disadvantages. For example, resveratrol, a polyphenol contained in grape skins, is known to be effective for mice fed with high-fat diet. In this process, sirtuin genes are reportedly activated.

Metformin, a therapeutic drug for diabetes mellitus, also has a life-extending effect. This drug is considered to increase the level of AMP-activated protein kinase. Also, rapamycin having an immunosuppressive effect has a life-extending effect. However, these drugs are expensive and might also cause adverse reactions by administration. Thus, there has been a demand for a substance that is inexpensive and has no adverse reaction (Non Patent Literatures 1 and 2).

CITATION LIST

Patent Literature

Patent Literature 1: Japanese Patent Laid-Open No. 2013-100323

Non Patent Literature

Non Patent Literature 1: Nature, 2009, 460, p. 392-395
Non Patent Literature 2: Nature Communication, 2003, DOI10.1038/ncomms3192
Non Patent Literature 3: J. Am. Chem. Soc., 1995, 117, p. 3278-3279

SUMMARY OF INVENTION

Technical Problem

Pyrroloquinoline quinone (hereinafter, also referred to as "PQQ") is a compound represented by the structural formula given below and has received attention as a useful substance for health supplements, cosmetics, and the like. The pyrroloquinoline quinone is known to form imidazolyl quinone through reaction with an amino acid (Non Patent Literature 3) and is thus not satisfactory in terms of stability.

(1)

The diverse physiologically active effects of PQQ revealed so far are mainly effects at the cell or tissue level. It has been unknown that PQQ is effective for the life extension of animal individuals. Also, it has been unknown that PQQ activates dual oxidase, which is NADPH oxidase. In addition, it has been unknown that the activation of the dual oxidase (NADPH oxidase) is effective for life extension, though this activation is generally considered to improve the amount of reactive oxygen species.

An object of the present invention is to provide, by using the PQQ, a novel life-extending agent, a life extension method using the life-extending agent, a novel dual oxidase activator, a method for activating dual oxidase, the production of a life-extending agent, and the production of a dual oxidase activator.

Solution to Problem

The present inventors have conducted diligent studies on the influence of PQQ on living bodies, particularly, the influence of PQQ on the life of living bodies. It is generally considered that when reactive oxygen species are generated, living bodies undergo oxidative stress, leading to aging or the shortening of life. For example, dual oxidase, which is NADPH oxidase, is known as a protein capable of producing reactive oxygen species (ROS). According to the previous finding that reactive oxygen species promote aging, the activation of dual oxidase seems to cause aging or the shortening of life. However, the present inventors have made studies using a nematode *C. elegans* serving as a model organism and consequently found that PQQ brings about life extension and this life extension is ascribable to the activation of dual oxidase (Bli-3). Specifically, the present inventors have gained the finding that PQQ activates dual oxidase (Bli-3) in the nematode individual so that longevity-inducing ROS is produced, and this works as a stimulus to enhance the host defense system, leading to life extension. The present invention has been made on the basis of these findings.

Specifically, the present invention is as given below.

[1]
A life-extending agent comprising pyrroloquinoline quinone and/or a derivative of the pyrroloquinoline quinone.

[2]
The life-extending agent according to [1], wherein each of the pyrroloquinoline quinone and the derivative of the pyrroloquinoline quinone is a compound represented by the following general formula (1), (2), or (3) or a salt thereof:

wherein each R independently represents a hydrogen atom or a substituent having 1 to 10 carbon atoms, and R' represents a substituent having 1 to 10 carbon atoms.

[3]
The life-extending agent according to [1] or [2], wherein the derivative of the pyrroloquinoline quinone comprises pyrroloquinoline quinone sodium salt.

[4]
The life-extending agent according to [3], wherein the pyrroloquinoline quinone sodium salt comprises crystals exhibiting 2θ 9.1±0.2°, 10.3±0.2°, 13.8±0.2°, and 24.0±0.2° by Cu-Kα radiation measurement in powder X-ray diffraction.

[5]
A life extension method using a life-extending agent according to any one of [1] to [4].

[6]
The life extension method according to [5], wherein the life of a human test subject or an animal is extended by administering the life-extending agent to the human test subject or the animal.

[7]
The life extension method according to [5] or [6], wherein the life of a human test subject or an animal is extended by administering the life-extending agent to the human test subject or the animal and thereby activating dual oxidase.

[8]
A dual oxidase activator comprising pyrroloquinoline quinone and/or a derivative of the pyrroloquinoline quinone.

[9]
The dual oxidase activator according to [8], wherein each of the pyrroloquinoline quinone and the derivative of the pyrroloquinoline quinone is a compound represented by the following general formula (1), (2), or (3) or a salt thereof:

wherein each R independently represents a hydrogen atom or a substituent having 1 to 10 carbon atoms, and R' represents a substituent having 1 to 10 carbon atoms.

[10]
The dual oxidase activator according to [8] or [9], wherein the derivative of the pyrroloquinoline quinone comprises pyrroloquinoline quinone sodium salt.

[11]
The dual oxidase activator according to [9], wherein the pyrroloquinoline quinone sodium salt comprises crystals exhibiting 2θ 9.1±0.2°, 10.3±0.2°, 13.8±0.2°, and 24.0±0.2° by Cu-Kα radiation measurement in powder X-ray diffraction.

[12]

A method for activating dual oxidase using a dual oxidase activator according to any one of [8] to [11].

[13]

Use of pyrroloquinoline quinone and/or a derivative of the pyrroloquinoline quinone for the production of a life-extending agent.

[14]

Use of pyrroloquinoline quinone and/or a derivative of the pyrroloquinoline quinone for the production of a life-extending agent that extends the life of a human test subject or an animal by the activation of dual oxidase.

[15]

Use of pyrroloquinoline quinone and/or a derivative of the pyrroloquinoline quinone for the production of a dual oxidase activator.

Advantageous Effects of Invention

The present invention can provide a novel life-extending agent, a life extension method using the life-extending agent, a novel dual oxidase activator, a method for activating dual oxidase, the production of a life-extending agent, and the production of a dual oxidase activator.

DESCRIPTION OF EMBODIMENTS

Hereinafter, the mode for carrying out the present invention (hereinafter, referred to as the "present embodiment") will be described in detail. However, the present invention is not intended to be limited by the present embodiment, and various changes or modifications can be made therein without departing from the spirit of the present invention.

[Life-Extending Agent]

The life-extending agent of the present embodiment comprises pyrroloquinoline quinone and/or a derivative of the pyrroloquinoline quinone. The life-extending agent of the present embodiment enables life extension, can prevent diseases associated with aging, has a strong pharmacological effect, and can produce an effective life-extending effect even without the use of ones having a high risk of adverse reactions.

In the present specification, the "life extension" refers to life extension that is induced by taking the substance of the present invention.

[Dual Oxidase Activator]

The dual oxidase activator of the present embodiment comprises pyrroloquinoline quinone and/or a derivative of the pyrroloquinoline quinone.

According to the findings of the present inventors, it has been revealed that after activation of dual oxidase, SKN-1 corresponding to nematode Nrf2 is activated via the p38 mitogen-activated protein kinase (p38MAPK) cascade.

Nrf2 is a mammalian transcriptional factor having a basic leucine zipper motif and is expressed in a wide range of organisms. Nrf2 usually resides in a form bound with Keap1 protein in the cytoplasm, but is translocated to the nucleus by the stimulation of an electrophilic substance or oxidative stress so that the Nrf2 forms a heterodimer with small Maf protein to induce the expression of a gene group related to detoxification or antioxidation. By this transcriptional activation, the Nrf2 complex binds to an antioxidant response element (ARE) commonly found in the promoter regions of the target gene group. The previous analysis of Nrf2-deficient mice, etc., suggests that the activation of Nrf2 contributes to the suppression of oncogenesis, liver damage, lung damage, inflammation, and the like. The structure and functions of Nrf2 are conserved across species. SKN-1 in the nematode *C. elegans* serving as a model organism corresponds to Nrf2.

Examples of the gene group whose transcription is targeted by the stress-responsive transcriptional factor Nrf2 include GCLM, GCLC, GSR, GSTA1, GPX1, GPX4, HMOX1, NQO1, SRXN1, SQSTM1, SOD1, UGT1A6, NOS2, NOS3, and PTGS2.

GCLM and GCLC: Glutamate cysteine ligase, also known as γ-glutamylcysteine ligase, is the first rate-limiting enzyme of glutathione (GSH) synthesis. This enzyme consists of two subunits (a heavy catalytic subunit (GCLC) and a light regulatory subunit (GCLM)). The overexpression of GCLC or GCLM in fruit-flies extends life without influencing the rate of oxygen consumption.

GSR: This gene encodes glutathione reductase (GSR), a member of the class I pyridine nucleoside-disulfide oxidoreductase family. This enzyme plays a central role in cellular antioxidant defense and reduces oxidized glutathione disulfide (GSSG) to a sulfhydryl form of GSH.

GSTA1: This gene encodes alpha class glutathione S-transferase which functions in detoxification based on the conjugation of GSH with electrophilic compounds including oncogenic substances, therapeutic drugs, environmental toxins, and products of oxidative stress. This enzyme metabolizes bilirubin and particular anticancer drugs in the liver. In addition, the alpha class glutathione S-transferase exhibits glutathione peroxidase activity and thereby protects cells from reactive oxygen species and peroxidation products.

GPX1: This gene encodes glutathione peroxidase which is an endogenous antioxidant enzyme responsible for the removal of toxic reactive oxygen species hydrogen peroxide ($H_2O_2$) and synthetic organic peroxides through the use of GSH as an electron donor.

GPX4: This gene encodes phospholipid hydroperoxide glutathione peroxidase which is an endogenous antioxidant enzyme having the same activity as that of GPX1 but further having the ability to remove metabolic toxins fatty acid hydroperoxide and cholesterol hydroperoxide.

SOD1: This gene encodes a soluble form of copper zinc superoxide dismutase (CuZnSOD1) which is an endogenous antioxidant enzyme involved in the catalytic removal of reactive superoxide radicals ($O_2^-$).

HMOX1: This gene encodes heme oxygenase (HO-1) which is an inducible isoform of the first and rate-limiting enzyme of heme decomposition. HO-1 also has a strong antioxidant function and anti-inflammatory function. The induction of HO-1 protects cells from cytotoxicity and apoptotic cell death by oxidative stress.

NQO1: This gene encodes cytoplasmic two-electron reductase, a member of the NAD(P)H dehydrogenase (quinone) family. Change in the expression of this protein is observed in many tumors and is also related to Alzheimer's disease (AD).

SRXN1: SRXN1 is an important molecule that undergoes transcriptional regulation by Nrf2 in protection against oxidative damage in the lung. When signal transduction involved in Nrf2 activation is reduced by RNAi in gene-knockout mouse individuals or a cultured cell system, the expression of SRNX1 is decreased. Computer analysis on the 5'-promoter-adjacent region of SRXN1 identified a plurality of highly conserved antioxidant response elements (AREs). Reporter and chromatin immunoprecipitation assays demonstrated that ARE1 at position −228 is important for transcriptional response based on Nrf2. The attenuation of SRXN1 expression by RNAi enhanced toxin sensitivity for $H_2O_2$, whereas the overexpression of SRXN1 protected cells from $H_2O_2$-mediated cell death in vitro.

UGT1A6: This gene encodes UDP-glucuronosyltransferase which is an enzyme of the glucuronidation pathway that converts small lipophilic molecules, for example, steroid, bilirubin, hormones, and drugs, to water-soluble excretable metabolites. The enzyme encoded by this gene has activity against phenolic and planar compounds.

NOS2: Nitrogen monoxide is a reactive free radical that acts as a biological mediator in some processes including neurotransmission as well as antimicrobial activity and antitumor activity. This gene encodes an inducible nitrogen monoxide synthase (iNOS) highly expressed in the liver.

NOS3: This gene encodes endothelium-derived NOS (eNOS) responsible for the production of nitrogen monoxide necessary for vasodilation and is abnormally regulated in an inflammatory state and aging.

PTGS2: Prostaglandin endoperoxide synthase (PTGS), also known as cyclooxygenase 2 (COX2), is an enzyme that plays a key role in prostaglandin biosynthesis, and acts as both dioxygenase and peroxidase. PTGS has two isozymes (constitutional PTGS1 and inducible PTGS2) which differ in the regulation of expression and tissue distribution. It is suggested that PTGS2 is responsible for prostanoid biosynthesis involved in inflammation and mitogenesis.

Among the molecular group whose transcription is controlled by Nrf2, GCLM, GCLC, and NOS3 are desirable in an aspect because of their remarkable physiological responses.

In the present specification, the "activation" refers to the upregulation of a particular factor. The "upregulation" refers to, for example, increase in the expression or activity of one or more genes and resulting protein(s) encoded by the gene(s) in response to a certain signal or agent.

[Pyrroloquinoline Quinone and Derivative Thereof]

Hereinafter, the pyrroloquinoline quinone and/or the derivative of the pyrroloquinoline quinone that can be used in the life-extending agent and the dual oxidase activator will be described in detail. Examples of the pyrroloquinoline quinone and the derivative thereof include, but are not particularly limited to, a compound represented by the following general formula (1), (2), or (3) and a salt thereof:

(1)

(2)

(3)

In the general formulas (1), (2), and (3), each R independently represents a hydrogen atom or a substituent having 1 to 10 carbon atoms, and R' represents a substituent having 1 to 10 carbon atoms.

Examples of the substituent having 1 to 10 carbon atoms represented by R include, but are not particularly limited to, alkyl and allyl. Among them, alkyl is preferred from the viewpoint of synthesis. The substituent having 1 to 10 carbon atoms represented by R may contain an oxygen atom, a nitrogen atom, a hydrogen atom, a sulfur atom, and/or a phosphorus atom, in addition to the carbon atoms.

[Compound Represented by General Formula (1) or Salt Thereof]

The compound of the general formula (1) where all of R are hydrogen atoms is called oxidized pyrroloquinoline quinone. Examples of the salt of the oxidized pyrroloquinoline quinone include, but are not particularly limited to, tricarboxylic acid, tricarboxylic acid di-salt, tricarboxylic acid mono-salt, and tricarboxylic acid tri-salt. Examples of the salt include, but are not particularly limited to: alkali metal salts such as lithium salt, sodium salt, and potassium salt; alkaline earth metal salts such as calcium salt, strontium salt, and barium salt; and salts with cationic compounds, such as ammonium salt and alkylammonium salt.

In the general formula (1), at least one R is preferably a hydrogen atom. The compound in which at least one R is a hydrogen atom is rendered ionic by forming a salt in a solution and therefore tends to have better water solubility than that of the form of tricarboxylic acid.

Examples of the compound represented by the general formula (1) or the salt thereof include, but are not particularly limited to: oxidized pyrroloquinoline quinone; and alkali metal salts of the oxidized pyrroloquinoline quinone, such as oxidized pyrroloquinoline quinone monosodium salt, oxidized pyrroloquinoline quinone disodium salt, oxidized pyrroloquinoline quinone trisodium salt, oxidized pyrroloquinoline quinone dipotassium salt, and oxidized pyrroloquinoline quinone tripotassium salt.

Among them, oxidized pyrroloquinoline quinone sodium salt such as oxidized pyrroloquinoline quinone monosodium salt, oxidized pyrroloquinoline quinone disodium salt, or oxidized pyrroloquinoline quinone trisodium salt is preferred from the viewpoint of easy availability.

[Compound Represented by General Formula (2) or Salt Thereof]

The compound represented by the general formula (2) or the salt thereof is a derivative of the pyrroloquinoline quinone. Examples of the substituent having 1 to 10 carbon atoms represented by R' include, but are not particularly limited to, an acetyl group, an ethoxy group, a ketoalkyl group, and a hydroxyalkyl group. Among them, an acetyl group or a ketoalkyl group is preferred from the viewpoint of stability. The substituent having 1 to 10 carbon atoms represented by R' may contain an oxygen atom, a nitrogen atom, a hydrogen atom, a sulfur atom, and/or a phosphorus atom, in addition to the carbon atoms.

Examples of the salt of the compound represented by the general formula (2) include, but are not particularly limited to, tricarboxylic acid, tricarboxylic acid di-salt, tricarboxylic acid mono-salt, and tricarboxylic acid tri-salt. Examples of the salt include, but are not particularly limited to: alkali metal salts such as lithium salt, sodium salt, and potassium salt; alkaline earth metal salts such as calcium salt, strontium salt, and barium salt; and salts with cationic compounds, such as ammonium salt and alkylammonium salt.

Examples of the compound represented by the general formula (2) or the salt thereof include, but are not particularly limited to, tricarboxylic acid, tricarboxylic acid disodium salt, tricarboxylic acid trisodium salt, tricarboxylic acid dipotassium salt, and tricarboxylic acid tripotassium salt in which R' is an acetyl group or an ethoxy group.

Among them, a derivative of the pyrroloquinoline quinone represented by the general formula (4) given below or a salt thereof (hereinafter, also referred to as an "acetone adduct") is preferred. Such a compound tends to be rarely deteriorated even in an environment containing an amino acid, etc.

(4)

[Compound Represented by General Formula (3) or Salt Thereof]

The compound of the general formula (3) wherein all of R are hydrogen atoms is called reduced pyrroloquinoline quinone formed by the reduction of the oxidized pyrroloquinoline quinone. Examples of the salt of the reduced pyrroloquinoline quinone include, but are not particularly limited to, tricarboxylic acid, tricarboxylic acid di-salt, tricarboxylic acid mono-salt, and tricarboxylic acid tri-salt. Examples of the salt include, but are not particularly limited to: alkali metal salts such as lithium salt, sodium salt, and potassium salt; alkaline earth metal salts such as calcium salt, strontium salt, and barium salt; and salts with cationic compounds, such as ammonium salt and alkylammonium salt.

In the general formula (3), at least one R is preferably a hydrogen atom. The compound of the general formula (3) wherein at least one R is a hydrogen atom is rendered ionic by forming a salt in a solution and therefore tends to have better water solubility than that of the form of tricarboxylic acid.

Examples of the compound represented by the general formula (3) or the salt thereof include, but are not particularly limited to: reduced pyrroloquinoline quinone; and alkali metal salts of the reduced pyrroloquinoline quinone, such as reduced pyrroloquinoline quinone monosodium salt, reduced pyrroloquinoline quinone disodium salt, reduced pyrroloquinoline quinone trisodium salt, reduced pyrroloquinoline quinone dipotassium salt, and reduced pyrroloquinoline quinone tripotassium salt.

Among them, reduced pyrroloquinoline quinone disodium such as reduced pyrroloquinoline quinone monosodium salt, reduced pyrroloquinoline quinone disodium salt, or reduced pyrroloquinoline quinone trisodium salt is preferred from the viewpoint of each production.

It is known that the compound represented by the general formula (1) has two quinones and therefore easily reacts with an amino acid and this reaction with an amino acid results in heterocyclic ring formation to form imidazoloquinone. On the other hand, the compound represented by the general formula (2) or (3) has one or no quinone and therefore tends to rarely react with an amino acid. Therefore, even when mixed with an amino acid in a state with a high temperature, the pyrroloquinoline quinone and the derivative thereof tend to be rarely decreased in level and to exhibit higher stability. Since media, foods, pharmaceutical products, etc., are rich in amino acid, it is preferred that the pyrroloquinoline quinone and the derivative thereof should rarely react with an amino acid. In addition, use of the compound represented by the general formula (2) or (3), which rarely reacts with an amino acid, tends to further improve the life-extending effect.

The phenolic hydroxy group of the compound represented by the general formula (2) is easily oxidized by oxygen in air to form quinone. Therefore, among the compounds represented by the general formulas (1), (2), and (3), the compound represented by the general formula (2) is more preferred, and the compound represented by the general formula (4) is further preferred, from the viewpoint of the life-extending effect

[Powder X-Ray Diffraction]

The pyrroloquinoline quinone sodium salt represented by the general formula (1) is preferably crystals exhibiting 2θ 9.1±0.2°, 10.3±0.2°, 13.8±0.2°, and 24.0±0.2° by Cu-Kα radiation measurement in powder X-ray diffraction. Use of such pyrroloquinoline quinone sodium salt tends to further improve stability. Such crystals can be obtained by a method described in, for example, Re-publication of PCT International Publication No. 2011/007633. The "pyrroloquinoline quinone sodium salt" means pyrroloquinoline quinone monosodium salt, pyrroloquinoline quinone disodium salt, and pyrroloquinoline quinone trisodium salt.

[Methods for Producing Pyrroloquinoline Quinone and Derivative Thereof]

Examples of the method for producing the pyrroloquinoline quinone include, but are not particularly limited to, an organic chemical synthesis method and a fermentation method. Among them, the fermentation method is a method for producing PQQ, for example, by culturing a bacterium having methanol utilization and having the ability to produce pyrroloquinoline quinone, using methanol as a carbon source.

The derivative of the pyrroloquinoline quinone, specifically, an ester form or the like of the pyrroloquinoline quinone or a salt of the pyrroloquinoline quinone, can be synthesized according to a routine method using the pyrroloquinoline quinone thus obtained as a starting material. The pyrroloquinoline quinone and the derivative thereof can each be separated and purified from the reaction solution by an ordinary method such as column chromatography, recrystallization, or solvent extraction. Also, the pyrroloquinoline quinone and the derivative thereof are each identified by use of various approaches including elemental analysis, NMR spectra, IR spectra, mass spectrometry, and the like.

[Purpose: Use of PQQ]

The present embodiment includes use of the pyrroloquinoline quinone and/or the derivative of the pyrroloquinoline quinone for the production of a life-extending agent, use of the pyrroloquinoline quinone and/or the derivative of the pyrroloquinoline quinone for the production of a life-extending agent that extends the life of a human test subject or an animal by the activation of dual oxidase, and use of the pyrroloquinoline quinone and/or the derivative of the pyrroloquinoline quinone for the production of a dual oxidase activator.

The life-extending agent or the dual oxidase activator can be used as a food, a functional food, a pharmaceutical product, or a quasi-drug for humans or for animals. In this context, the functional food means a food that is taken for the purpose of health maintenance or nutritional support as a substitute for diet, for example, health foods, nutritional supplements, foods with nutrient function, and foods for specified health uses. Examples of the specific form thereof include, but are not limited to, capsules, tablets, chewables, tablets, and drinks.

For the pharmaceutical purpose, the life-extending agent or the dual oxidase activator can be used by a method such as oral administration, injection, or dermal absorption. In the case of oral administration, the life-extending agent or the dual oxidase activator can be mixed with other substances and used in the form of a hard capsule, a soft capsule, or a tablet. Alternatively, the life-extending agent or the dual oxidase activator may be used as a drink, an infusion, or an injection solution through the use of its high water solubility. In addition, the life-extending agent or the dual oxidase activator can be mixed with an emulsion and contained in a cosmetic cream or cake, or can be used in a food based on rice or wheat flour because of easy mixing therewith.

In the case of using the life-extending agent or the dual oxidase activator for a nematode, for example, a method of mixing the life-extending agent or the dual oxidase activator into a medium is used. Specifically, the life-extending agent or the dual oxidase activator is dissolved in a medium containing peptone rich in amino acid, cholesterol, and inorganic ions, and the life-extending agent or the dual oxidase activator is orally absorbed to the nematode via feed *E. coli* growing in this state, or percutaneously absorbed thereto from the medium. The amount of the life-extending agent or the dual oxidase activator mixed into the medium is preferably 1 to 100 mM, more preferably 1 to 20 mM, further preferably 1 to 15 mM, still further preferably 1 to 5 mM.

In the case of using the life-extending agent or the dual oxidase activator for an animal, the dose thereof varies depending on the recipient animal. When the recipient animal is a human, the dose thereof varies depending on various factors such as a target disease, the age, sex, or body weight of the patient, the severity of symptoms, and an administration route. When the recipient animal is a human, typically 0.25 to 1000 mg, preferably 1 to 250 mg, more preferably 10 to 100 mg, of the life-extending agent or the Nrf2 activator per day is administered to an adult having a body weight of approximately 60 kg. The life-extending agent or the Nrf2 activator can be administered one or more times a day.

[Life Extension Method]

The life extension method of the present embodiment uses the life-extending agent described above and preferably uses the compound represented by the general formula (1), (2), or (3) or the salt thereof. In the present invention, the life-extending effect is effective for eukaryotes, preferably animals.

The life extension method of the present embodiment can extend life and can further protect an organism from aging-related diseases. Also, the life extension method of the present embodiment can extend the life of an organism and delay the development of complications related to aging-related diseases.

Specific examples of the method include, but are not particularly limited to, a method comprising administering the life-extending agent to an animal or a patient for the purpose of treatment or procedure by the method as described in the paragraph [Purpose]. In short, examples thereof include a method comprising extending the life of a human test subject or an animal by administering the life-extending agent to the human test subject or the animal, more specifically, a method comprising extending the life of a human test subject or an animal by administering the life-extending agent to the human test subject or the animal and thereby activating dual oxidase.

In the present specification, the "animal" or the "patient" can refer to vertebrates such as birds, fish, and mammals, and invertebrates such as insects and nematodes. When the life extension method of the present embodiment corresponds to a treatment method, humans are excluded from the recipient animal.

In the present specification, examples of the "treatment" or the "procedure" include, but are not particularly limited to:

the procedure of a pathological condition in a mammal, comprising (a) a step of preventing the pathological condition in the mammal, specifically, when such a mammal is more likely to have the pathological condition but has not been diagnosed with the pathological condition;

(b) a step of suppressing the pathological condition, for example, a step of stopping the progression thereof; and/or (c) a step of mitigating the pathological condition, for example, a step of causing the regression of the pathological condition to reach a desired endpoint. The treatment also includes recovery from a symptom of a disease (e.g., alleviation of pain or discomfort). Such recovery may or may not have a direct effect on the disease (e.g., cause, transmission, or manifestation).

[Dual Oxidase Activation Method]

The dual oxidase activation method of the present embodiment uses the pyrroloquinoline quinone and/or the derivative of the pyrroloquinoline quinone (dual oxidase activator) and preferably uses the compound represented by the general formula (1), (2), or (3) or the salt thereof.

Specific examples of the method, include, but are not particularly limited to, a method comprising using (administering) the dual oxidase activator to an animal by the method as described in the paragraph [Purpose].

One manner in which the process of aging can appear at the organism level is change in the ability to respond to oxidative stress and electrophilic damage, which bring about increase in cellular injury. This change caused by aging occurs at the levels of various cells that constitute tissues and contribute to their functions in the organ system. The activity, structures, and identities of cells are derived from specific proteins regulated by gene expression. Therefore, the fundamental age-related change in the structures and functions of cells can also be found in change in gene expression.

Thus, the dual oxidase activation method is effective for the suppression of diseases caused by aging, in addition to the life-extending effect. More specifically, the dual oxidase activation method is effective for all of diseases whose risk factor is probably aging. Examples of such diseases include, but are not particularly limited to, Alzheimer's disease, Parkinson's disease, myocardial infarction, and diabetes mellitus.

The dual oxidase activation method is also used for preventing or treating diseases or disorders related to the expression and/or function of dual oxidase or the expression and/or function of Nrf2. In this context, the diseases or the disorders include diseases or disorders related to the abnormal expression and/or function of a dual oxidase variant or normal dual oxidase or a Nrf2 variant or normal Nrf2. Particularly, Nrf2 is a transcriptional factor that responds to the redox state of an adult or cells, and upregulates a series of antioxidative genes and cytoprotective enzymes constituting defense against oxidative stress. The regulation of Nrf2 is important for the treatment of diseases or disorders related to oxidative stress.

Examples of the target diseases and disorders of the present embodiment include, but are not particularly limited to, chronic obstructive pulmonary disease (COPD), multiple sclerosis, liver diseases or disorders, gastrointestinal diseases or disorders, diabetes mellitus, diseases or disorders related to autoimmune or immune, immunodeficiency (e.g., AIDS), neurological diseases or disorders, neurodegenerative diseases or disorders, diseases or disorders or conditions related to oxidative stress, eye diseases (e.g., age-related macular degeneration, cataract, photoretinopathy, and retinopathy of prematurity), skin diseases, asthma, arteriosclerosis, chronic inflammatory diseases or conditions (e.g., angiitis, pulmonary or bronchial inflammation, rheumatoid arthritis, osteoarthrosis, hepatitis, pancreatitis, dermatitis, esophagitis, ulcerative colitis, Crohn's disease, and conjunctivitis), neural repair and paralysis, neuroendocrine differentiation, inflammatory diseases, muscular diseases or disorders, diseases or disorders related to infective organisms, senile plaques, cerebral amyloid angiopathy, atherosclerosis, glioblastoma, amyloid deposition, neurofibrillary tangle, dementia, choriocarcinoma, astrocytoma, amyloidosis, hyperlipidemia, malignant transformation, arteriosclerotic lesions, atherosclerotic occlusion, metastasis, myocardial infarction, pulmonary fibrosis, necrosis, shock, melanoma, colorectal cancer, genetic susceptibility, psoriasis, diseases or disorders related to abnormal cell growth (e.g., cancer and psoriasis), cancer (e.g., prostate cancer, lung cancer, breast cancer, non-small cell lung cancer (NSCLC), and leukemia), inflammation, glioma, carcinoma, neuropathological conditions, tumors, vascular diseases, cytotoxicity, brain tumor, hypercholesterolemia, liposarcoma, coronary heart diseases, coronary diseases, glomerulonephritis, phlebothrombosis, hypothyroidism, and pathological processes.

The term "cancer" used in the present specification means any malignant tumor, specifically, a malignant tumor occurring in the lung, the kidney, or the thyroid gland. The cancer appears as a tissue including malignant cells of "tumor" or cancer. Examples of the tumor include, but are not limited to, sarcomas and cancers such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic carcinoma, breast carcinoma, ovarian carcinoma, prostate carcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic lung carcinoma, renal cell carcinoma, hepatoma, bile duct carcinoma, choriocarcinoma, seminoma, embryonal carcinoma, Wilms' tumor, cervical carcinoma, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. The "cancer", the "neoplasm", and the "tumor" used in the present specification are interchangeably used and, in either singular or plural forms, mean cells that have been malignantly transformed to be pathogenic in host organisms. Primary cancer cells (i.e., cells obtained from a malignant transformation site or its neighborhood) can be easily distinguished from noncancer cells by a well-established technique, specifically, a histological test. The definition of the cancer cells used in the present specification includes not only the primary cancer cells but any cell derived from cancer cell progenitors. This includes metastasized cancer cells, and in vitro cultures and cell lines derived from cancer cells. In the case of cancer that usually appears as a solid tumor, the "clinically detectable" tumor is a tumor that can be detected on the basis of tumor mass by procedures such as CAT scan, nuclear magnetic resonance imaging, X-ray, ultrasonic wave, or palpation, and/or a tumor that can be detected from the expression of one or more cancer-specific antigens in a sample obtained from a patient.

The "neurological diseases or disorders" mean any disease or disorder of the nervous system and/or the visual system. The "neurological diseases or disorders" include diseases or disorders related to the central nervous system (brain, brain stem, and cerebellum), the peripheral nervous system (including cerebral nerve), and the autonomic nervous system (a portion of which is positioned in both of the central nervous system and the peripheral nervous system). Examples of the neurological diseases or disorders include, but are not limited to: acquired epileptic aphasia; acute disseminated encephalomyelitis; adrenoleukodystrophy; age-related macular degeneration; agenesis of corpus callosum; agnosia; Aicardi's syndrome; Alexander disease; Alpers' disease; alternating hemiplegia; Alzheimer's disease; vascular dementia; amyotrophic lateral sclerosis; anencephaly; Angelman's syndrome; angiomatosis; anoxia; aphasia; apraxia; arachnoid cyst; arachnoiditis; Arnold-Chiari malformation; arteriovenous malformation; Asperger's syndrome; ataxia telangiectasia; attention-deficit hyperactivity disorder; autism; dysautonomia; back pain; Batten disease; Behcet's disease; Bell's palsy; benign essential blepharospasm; benign lesions; amyotrophy; benign intracranial hypertension; Binswanger's disease; blepharospasm; Bloch-Sulzberger syndrome; injury to the brachial plexus; brain abscess; brain injury; brain tumor (including glioblastoma multiforme); spine tumor; Brown-Sequard syndrome; Canavan disease; carpal-tunnel syndrome; burning pain; central pain syndrome; central pontine myelinolysis; disorders of the head; brain aneurysm; brain arteriosclerosis; cerebral atrophy; cerebral gigantism; cerebral palsy; Charcot-Marie- Tooth disease; chemotherapy-induced neuropathy and neuropathic pain; Chiari malformation; chorea; chronic inflammatory demyelinating neuropathy; chronic pain; chronic local pain syndrome; Coffin-Lowry syndrome; coma including persistent vegetative state; congenital facial paraplegia; corticobasal degeneration; cranial arteritis; craniosynostosis; Creutzfeldt-Jakob disease; cumulative trauma disorder; Cushing syndrome; cytomegalic inclusion disease; cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; alexia; dystonia; Early infantile epileptic encephalopathy; Empty sella syndrome; encephalitis; encephalocele; encephalotrigeminal angiomatosis; epilepsy; Erb's palsy; essential tremor; Fabry disease; fahr's syndrome; syncope; familial spastic paraplegia; heat cramp; Fisher syndrome; Friedreich's ataxia; frontotemporal dementia and other "tauopathies; Gaucher's disease; Gerstmann syndrome; giant-cell arteritis; giant cell inclusion body disease; globoid-cell leukodystrophy; Guillain-Barre syndrome; HTLV-1-associated myelopathy; Hallervorden-Spatz syndrome; head injury; headache; hemifacial spasm; hereditary spastic paraplegia; heredopathia atactica polyneuritiformis; herpes zoster oticus; herpes zoster; Hirayama syndrome; HIV-associated dementia and HIV-associated neuropathy (also including neurological symptoms of AIDS); holoprosencephaly; Huntington's disease and other polyglutamine-repeat diseases; hydranencephaly; hydrocephalus; hypercortisolism; hypoxia; immune-mediated encephalomyelitis; inclusion body myositis; incontinence of pigment; infant phytanic acid storage disease; infantile Refsum's disease; epilepsia nutans; inflammatory myopathy; intracranial cyst; intracranial hypertension; Joubert syndrome; Kearns-Sayre syndrome; Kennedy disease; Kinsbourne syndrome; Klippel-Feil syndrome; Krabbe disease; Kugelberg-Welander disease; Kuru; Lafora disease; Lambert-Eaton syndrome; Landau-Kleffner syndrome; Lateral medullary (Wallenberg) syndrome; learning disability; Leigh disease; Lennox-Gastaut syndrome; Lesch-Nyhan syndrome; leukodystrophy; dementia with Lewy bodies; agyria; locked-in syndrome; Lou Gehrig's disease (i.e., motoneuron disease or amyotrophic lateral sclerosis); lumbar disc disease; Lyme disease-neurological sequelae; Machado-Joseph disease; megalencephaly; macrencephaly; Melkersson-Rosenthal syndrome; Meniere disease; meningitis; Menkes disease; metachromatic leukodystrophy; microcephaly; migraine; Miller Fisher syndrome; petit mal seizure; mitochondrial myopathy; Mobius syndrome; monomelic muscular atrophy; motoneuron disease; moyamoya disease; mucopolysaccharidosis; multi-infarct dementia; multifocal motor neuropathy; multiple sclerosis and other demyelinating diseases; multiple system atrophy with postural hypotension; muscular dystrophy; myasthenia gravis; myelinoclastic diffuse sclerosis; infantile myoclonic encephalopathy; myoclonus; myopathy; congenital myotonia; narcolepsy; neurofibromatosis; neuroleptic malignant syndrome; neurological symptoms of AIDS; neurological sequelae of lupus; neuromyotonia; neuronal ceroid lipofuscinosis; neuronal migration disorder; Niemann-Pick disease; O'Sullivan-McLeod syndrome; occipital neuralgia; frequent occurrence of occult spinal dysraphism; Ohtahara syndrome; olivopontocerebellar atrophy; opsoclonus-myoclonus ataxia; optic neuritis; orthostatic hypotension; overuse syndrome; dysesthesia; neurodegenerative diseases or disorders (Parkinson's disease, Huntington disease, Alzheimer's disease, amyotrophic lateral sclerosis (ALS), dementia, multiple sclerosis, and other diseases or disorders related to neuronal death); congenital paramyotonia; paraneoplastic diseases; seizure; Parry-Romberg syndrome; Pelizaeus-Merzbacher disease; periodic paralysis; peripheral neuropathy; painful neuropathy and neuropathic pain; persistent vegetative state; pervasive development disorder; photic sneeze reflex; phytanic acid storage disease; Pick disease; pinched nerve; pituitary gland tumor; multiple myositis; porencephaly; post-polio syndrome; postherpetic neuralgia; postinfectious encephalomyelitis; postural hypotension; Prader-Willi syndrome; primary lateral sclerosis; prion disease; progressive unilateral facial atrophy; progressive multifocal leukoencephalopathy; progressive sclerosing poliodystrophy; progressive supranuclear palsy; pseudotumor cerebri; Ramsay Hunt syndrome (type I and type II); Rasmussen's encephalitis; reflex sympathetic dystrophy syndrome; Refsum's disease; repetitive motion disorder; repetitive stress injury; restless legs syndrome; retrovirus-associated myelopathy; Rett syndrome; Reye's syndrome; chorea; Sandhoff's disease; Schilder disease; schizencephaly; septo-optic dysplasia; shaken baby syndrome; herpes zoster; Shy-Drager syndrome; Sjogren's syndrome; sleep apnea; Sotos syndrome; contracture; spina bifida; spinal cord injury; spinal cord tumor; spinal muscular atrophy; stiff-person syndrome; stroke; Sturge-Weber syndrome; subacute sclerosing panencephalitis; subcortical arteriosclerotic encephalopathy; Sydenham's chorea; syncope; syringomyelia; tardive dyskinesia; Tay-Sachs disease; temporal arteritis; tethered cord syndrome; Thomsen disease; thoracic outlet syndrome; painful tic; Todd's paralysis; Tourette syndrome; transient ischemic attack; transmissible spongiform encephalopathy; transverse myelitis; traumatic brain injury; tremor; trigeminal neuralgia; tropical spastic paraparesis; nodular sclerosis; vascular dementia (multi-infarct dementia); angiitis including temporal arteritis; Von Hippel-Lindau disease; Wallenberg-Syndrome; Werdnig-Hoffmann disease; West syndrome; whiplash; Williams syndrome; Wilson disease; and Zellweger syndrome.

EXAMPLES

Hereinafter, the present invention will be described more specifically with reference to Examples and Comparative Examples. The present invention is not intended to be limited by Examples below by any means.

The PQQ disodium salt used in the present Examples was BioPQQ manufactured by Mitsubishi Gas Chemical Company, Inc. The other compounds used were reagents manufactured by Wako Pure Chemical Industries, Ltd. unless otherwise specified.

[Cu-Kα Radiation Measurement in Powder X-Ray Diffraction]

The Cu-Kα radiation measurement in powder X-ray diffraction of PQQ disodium salt was performed under conditions shown below. As a result, the PQQ disodium salt was crystals exhibiting 2θ 9.1°, 10.3°, 13.8°, and 24.0°.

(Measurement Conditions)

Apparatus: RINT2000 manufactured by Rigaku Corp.
X-ray: Cu/tube voltage of 40 kV/tube current of 100 mA
Incident slit: ⅔°
Scattering slit: ⅔°
Receiving slit: 0.3 mm
Scan speed: 4.000°/min
Sampling width: 0.02

[Ultraviolet-Visible (UV) Spectrum Analysis]

Ultraviolet-visible spectra were measured using a UV spectrometer UV1800 manufactured by Shimadzu Corp.

[PQQ Analysis]

The analysis of PQQ sodium salt was conducted under analysis conditions given below. PQQ concentration and purity were measured by high-performance liquid chromatography under conditions shown below.

(Measurement Conditions)

Apparatus: high-performance liquid chromatography, LC-2010 manufactured by Shimadzu Corp.
Column: YMC-Pack ODS-A, 150×4.6 mm I.D.
Measurement temperature: 40° C.
Detection: absorbance at 259 nm
Eluent: 30 mM acetic acid/70 mM ammonium acetate (pH 5.1)
Elution rate: 1.5 mL/min Next, Na concentration contained in the same solution was measured using a sodium electrode manufactured by HORIBA, Ltd.

Also, the amount-of-substance ratio between PQQ and Na contained in the PQQ sodium salt was determined from the concentrations of PQQ and Na contained in the solution described above. When this amount-of-substance ratio was 2.0±0.2, the salt was confirmed to be PQQ disodium salt. When the amount-of-substance ratio was 3.0±0.2, the salt was confirmed to be PQQ trisodium salt.

Production Example 1: Reduced Pyrroloquinoline Quinone

5 g of PQQ disodium salt (BioPQQ manufactured by Mitsubishi Gas Chemical Company, Inc.) and 1 L of water were mixed, and the obtained aqueous solution was warmed to 70° C. This aqueous solution was mixed with a mixed solution containing 50 g of ascorbic acid and 0.2 L of water. The obtained aqueous solution was reacted at 70° C. for 3 days. Then, 10 mL of 2 N hydrochloric acid was added thereto, and the aqueous solution was reacted for 2 hours. Then, the temperature was brought back to room temperature, and the solid deposited in the aqueous solution was filtered and washed with 2 N hydrochloric acid and ethanol. The obtained solid was dried under reduced pressure to obtain 3.6 g of reduced pyrroloquinoline quinone represented by the following general formula (4) as a solid.

(4)

Production Example 2: Acetone Adduct of Pyrroloquinoline Quinone

11.2 g of PQQ disodium salt (BioPQQ manufactured by Mitsubishi Gas Chemical Company, Inc.) and 1 L of water were mixed, and sodium hydroxide was added thereto to obtain an aqueous solution of pH 9. 200 g of acetone was added to the obtained aqueous solution. As a result, the color of the aqueous solution was changed from red to pale yellow in 20 minutes. The pH of the aqueous solution thus color-changed was adjusted to 2.5 by the addition of hydrochloric acid. The solvent was distilled off from the aqueous solution, and the residue was concentrated until the total weight became 400 g. The yellow solid deposited in the concentrated aqueous solution was dried under reduced pressure to obtain 8.01 g of an acetone adduct of pyrroloquinoline quinone represented by the following general formula (5) as a solid.

(5)

Production Example 3: Imidazoloquinone 100 g of PQQ disodium salt (BioPQQ manufactured by Mitsubishi Gas Chemical Company, Inc.), 200 g of glycine, and 0.5 L of water were mixed to obtain an aqueous solution of pH 4.8. The obtained aqueous solution was stirred for 30 minutes. As a result, bubbles were developed so that the aqueous solution was solidified. The obtained mixture was heated to 70° C. and reacted for 3 days. Then, 1000 g of water containing 10% by mass of NaCl was added to the mixture, and the solid was filtered. The solid thus obtained by filtration was mixed with 120 g of water containing 25% by mass of NaOH and 30 g of water to obtain an aqueous solution of pH 10.8. The obtained aqueous solution was warmed to 70° C. and left overnight. Then, the deposited solid was filtered and washed with 2-propanol and further with 400 mL of ethanol. The obtained solid, 500 mL of water, and 41.5 g of NaOH were mixed to obtain an aqueous solution of pH 10.3. The obtained aqueous solution was left standing overnight at 70° C. Then, the aqueous solution was cooled in ice, and the deposited solid was filtered and washed with 2-propanol. The obtained solid was dried under reduced pressure at 70° C. to obtain 65.8 g of a solid. The obtained solid was analyzed by LC and Na ion analysis to confirm that the solid was trisodium salt of imidazoloquinone (hereinafter, also referred to as IPQ) represented by the following general formula (6).

Examples 1 to 4 and Comparative Example 1: Pyrroloquinoline Quinone Disodium Salt

[Life Test]
[Preparation of Medium for Nematode]

Pyrroloquinoline quinone disodium salt was mixed with water and sodium hydroxide to obtain test sample concentrate 1 of pH 6.

The content of the pyrroloquinoline quinone disodium salt in the test sample concentrate 1 was adjusted to 30 mM. The test sample concentrate 1 was autoclave-sterilized for use.

7.2 g of NaCl, 48 g of agar, 6 g of Bactopeptone (manufactured by Becton, Dickinson and Company), and water (2.4 L including the amount of the sample concentrate to be added) were added into each flask. The flask was autoclaved at 120° C. for 20 minutes or longer and then cooled until the surface temperature of the flask became approximately 45° C. To this flask, 60 mL of a 1 M potassium phosphate solution, 2.4 mL of a 1 M $CaCl_2$ solution, 2.4 mL of a 1 M $MgSO_4$ solution, 2.4 mL of a 750 mg/150 mL cholesterol solution, and a predetermined amount of the 30 mM test sample concentrate 1 were added to obtain a medium solution. The amount of the test sample concentrate 1 added was adjusted such that the concentration of the pyrroloquinoline quinone disodium salt in the medium solution was 0 mM (Comparative Example 1), 0.1 mM (Example 1), 1.0 mM (Example 2), 3.0 mM (Example 3), and 5.0 mM (Example 4). The flask was further cooled until the surface temperature of the flask reached 40 to 41° C. 14 mL of the medium solution was added to each polystyrene petri dish having a diameter of 6 cm and cooled to room temperature to prepare petri dishes having media containing different concentrations of the pyrroloquinoline quinone disodium salt.

Meanwhile, to each *E. coli* solution cultured in an LB medium (Luria-Bertani broth), the test sample concentrate 1 was added so as to attain the same concentration as that of the pyrroloquinoline quinone disodium salt in the medium of each of the prepared petri dishes. 100 µL of the obtained *E. coli* solution was seeded in a circular pattern of approximately 2 cm in diameter to the center of each petri dish. This petri dish was preserved at normal temperature and used in the nematode test described below 2 to 4 days after the preparation.

[Nematode Test]
(Synchronization (Adjustment of Age))

In order to synchronize the ages of nematode individuals at the start of the experiment, parent nematodes were allowed to lay eggs and then removed, and individuals evenly grown for a given period of time after hatching were used. Specifically, five adults (individuals under incubation) were selected and transferred to each petri dish, which was then left at 20° C. for 2 hours (lay period), and the parent nematodes were removed. Then, the petri dish was left at 20° C. for 72 hours. The life test was started when the number of individuals per petri dish reached 10 to 20. The rearing at a density as low as 10 to 20 individuals per petri dish decreased influence derived from a shortage of feed or the accumulation of excrement.

As for experiments using various mutants, a stage was determined on the basis of the degree of development of the genital organ because the emergence rate of many mutants was slower than that of the wild-type line. Grown-up individuals were used in the life assay.

(Life Assay (Life Measurement))

The individuals in each petri dish were transferred to a fresh petri dish every day. Information on date, the number of survivors, the number of deaths, the number of missing individuals, etc., was recorded in a score sheet. The petri dish was wrapped in Parafilm during storage. An individual was judged as being dead when no spontaneous behavior was seen and no response was found even by vibration stimulus or contact stimulus. Nematodes are often missing because of running out of the petri dish, being dried at the wall, crawling out from a gap in the medium, for example. Therefore, the number of missing individuals was recorded and excluded from the data. Individuals that died of the eclosion of their children in their bodies, which occurs frequently in certain variants, were recorded as BAG, and individuals that died of hernia were recorded as rupture. These individuals were excluded from the data. The results of measurement at the varying concentrations of the pyrroloquinoline quinone disodium salt in the media are shown in FIGS. 1 and 2.

Figure 1:
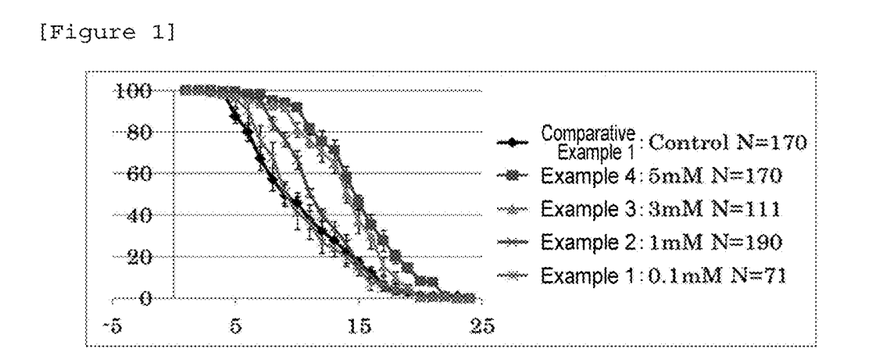
FIG. 1 is a graph showing results of a life test in Examples 1 to 4 and Comparative Example 1.
Figure 2:
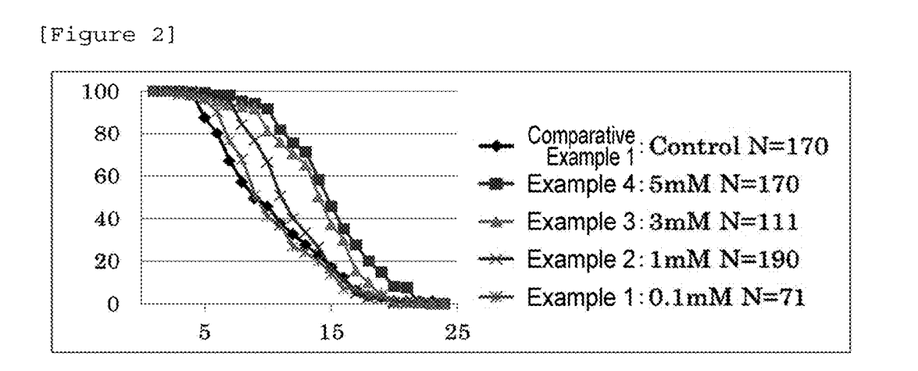
FIG. 2 is a graph showing results of a life test in Examples 1 to 4 and Comparative Example 1.

As shown in FIGS. 1 and 2, a higher concentration of the pyrroloquinoline quinone disodium salt tends to extend the average life. The ordinates of FIGS. 1 and 2 depict the survival rate of the nematode, and the abscissas depict the number of rearing days (life) after becoming adults. Standard deviation is given at the foot of the graph. In FIGS. 1 and 2, N denotes the number of nematodes at the time of testing. The same holds true for FIGS. 3 and 4 below.

Example 5 and Comparative Example 2: Acetone Adduct

The acetone adduct prepared in Production Example 2 was mixed with sodium bicarbonate having the same weight thereas, and sterile water to obtain test sample concentrate 2. The content of the acetone adduct in the test sample concentrate 2 was adjusted to 30 mM.

Petri dishes having media containing different concentrations of the acetone adduct were prepared by the same operation as in Example 1 except that the amount of the test sample concentrate 2 added was adjusted such that the concentration of the acetone adduct in each medium solution was 0 mM (Comparative Example 2) and 5.0 mM (Example 5). Then, the life test was conducted in the same way as in Example 1. The results are shown in FIG. 3.

Figure 3:
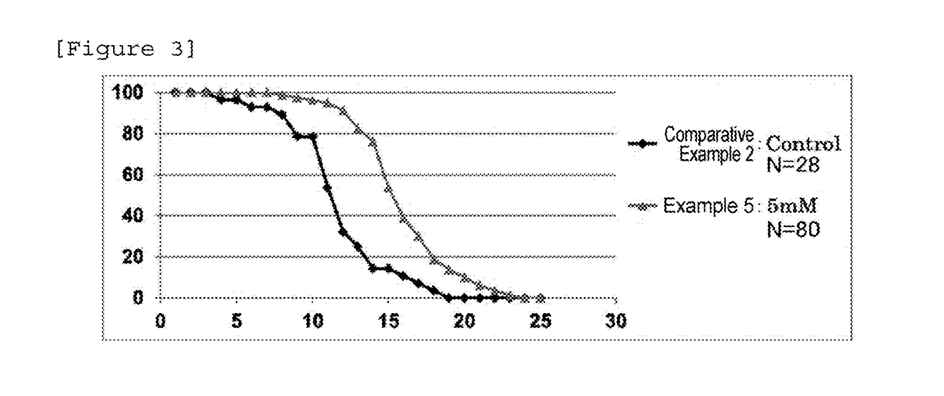
FIG. 3 is a graph showing results of a life test in Example 5 and Comparative Example 2.

As shown in FIG. 3, the inclusion of the acetone adduct tends to extend the average life.

Comparative Examples 3 and 4: IPQ Trisodium Salt

The IPQ trisodium salt prepared in Production Example 3 was mixed with water to obtain test sample concentrate 3. The content of the IPQ trisodium salt in the test sample concentrate 3 was adjusted to 30 mM. The test sample concentrate 3 was autoclave-sterilized for use.

Figure 4:
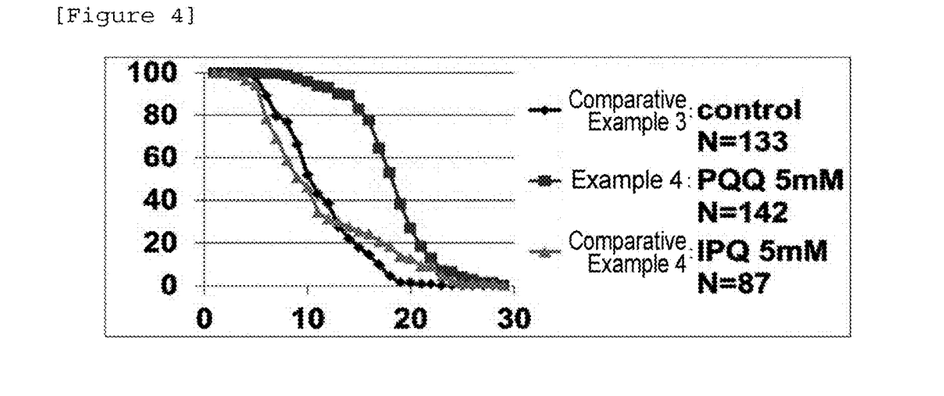
FIG. 4 is a graph showing results of a life test in Comparative Examples 3 and 4.

Petri dishes having media containing different concentrations of the IPQ trisodium salt were prepared by the same operation as in Example 1 except that the amount of the test sample concentrate 3 added was adjusted such that the concentration of the IPQ trisodium salt in each medium solution was 0 mM (Comparative Example 3) and 5.0 mM (Comparative Example 4). Then, the life test was conducted in the same way as in Example 1. The results are shown in FIG. 4. FIG. 4 also shows the data on Example 4.

Examples 6 and 7 and Comparative Example 5: Stability of Test Substance

The reduced pyrroloquinoline quinone, the acetone adduct of pyrroloquinoline quinone, and the IPQ trisodium salt in the petri dishes used in the life test were evaluated for their stability by liquid chromatography analysis (LC analysis). The results are shown in Table 1. The liquid chromatography analysis can be conducted according to those described above.

Example 8: Stability of Reduced PQQ

Reduced PQQ was added to sterile water to prepare a 30 mM dispersion. This dispersion was added so as to make 5 mM in the composition for evaluation described above to prepare a petri dish. The preservation test was conducted at 30° C. for 3 days, followed by LC analysis and UV spectrum analysis. The reduced formed is converted to PQQ under neutral conditions. Therefore, the reduced state can be confirmed by detecting PQQ by the LC analysis and measuring the UV spectrum of a solution thereof in dimethyl sulfoxide. As a result of confirming the state of the reduced PQQ in an agar medium in this way, 86% of all PQQs maintained the reduced state.

TABLE 1

| | Test substance (%) | Main impurities |
|---|---|---|
| Example 6 | Reduced pyrroloquinoline quinone 65% | IPQ |
| Example 7 | Acetone adduct of pyrroloquinoline quinone 92% | PQQ |
| Example 8 | Reduced pyrroloquinoline quinone 85% | PQQ |
| Comparative Example 5 | IPQ100% | — |

E. coli colonies in the petri dishes used in Examples 1 to 5 were taken out and subjected to extraction and analysis by the same operation as in the medium analysis. Each test substance was also detected as a primary component from the E. coli used in the test.

The PQQ produced in Example 1 is converted to IPQ through reaction with amino acids in the peptone. However, as shown in Comparative Example 1, IPQ has a small life-extending effect, demonstrating that PQQ is an active ingredient. IPQ, which is easily generated, was not detected by the formation of the acetone adduct, demonstrating that the stability was improved.

Examples 9 to 18 and Comparative Examples 6 to 15: Life Test Using Variant

Nematode variants can be used to determine how PQQ works. A plurality of petri dishes were prepared using the medium containing 5 mM PQQ prepared in Example 4. The life extension test was conducted in the same way as in Example 1 using the prepared petri dishes and each variant shown in Table 2. The results are summarized in Table 2 below. The results obtained without the addition of PQQ are indicated as 100 for a relative effect. Table 2 shows the life extension by 5 mM PQQ after becoming adults.

TABLE 2

| | Variant | Use of PQQ | Average life after becoming adult (day) | Relative value |
|---|---|---|---|---|
| Example 9 | wild-type | Present | 15.0 ± 0.6 | 140 |
| Comparative Example 6 | wild-type | Absent | 10.7 ± 0.4 | 100 |
| Example 10 | daf-2 (e1370) | Present | 34.6 ± 0.9 | 121 |
| Comparative Example 7 | daf-2 (e1370) | Absent | 28.7 ± 1.3 | 100 |
| Example 11 | age-1 (hx546) | Present | 23.4 ± 0.9 | 123 |
| Comparative Example 8 | age-1 (hx546) | Absent | 19.1 ± 0.6 | 100 |
| Example 12 | skn-1 (zu67) | Present | 12.8 ± 0.2 | 96 |
| Comparative Example 9 | skn-1 (zu67) | Absent | 13.3 ± 0.5 | 100 |
| Example 13 | gas-1 (fc2) | Present | 14.7 ± 0.9 | 111 |
| Comparative Example 10 | gas-1 (fc2) | Absent | 13.3 ± 0.7 | 100 |
| Example 14 | bli-3 (e767) | Present | 13.5 ± 0.4 | 87 |
| Comparative Example 11 | bli-3 (e767) | Absent | 15.5 ± 0.4 | 100 |
| Example 15 | OB265bli-3 (e767); imEx144[bli-3genomic clone] | Present | 19.8 ± 0.3 | 122 |
| Comparative Example 12 | OB265bli-3 (e767); imEx144[bli-3genomic clone] | Absent | 16.2 ± 0.3 | 100 |
| Example 16 | pmk-3 (ok-169) | Present | 17.9 ± 0.4 | 90 |
| Comparative Example 13 | pmk-3 (ok-169) | Absent | 19.8 ± 0.4 | 100 |
| Example 17 | bli-3 (im-10) | Present | 11.7 ± 0.4 | 99 |
| Comparative Example 14 | bli-3 (im-10) | Absent | 11.8 ± 0.5 | 100 |
| Example 18 | nsy-1 (ky400) | Present | 16.0 ± 0.3 | 104 |
| Comparative Example 15 | nsy-1 (ky400) | Absent | 15.4 ± 0.3 | 100 |

In Examples 14 and 17, the life-extending effect of PQQ was not observed in the lines with functional decline of the bli-3 gene. By contrast, the life of the bli-3 gene-deficient line transfected with the bli-3 gene in Example 15 was extended by the addition of PQQ, and the phenotype causing no life extension by PQQ was rescued. These results indicate that the bli-3 gene is a gene useful in the achievement of longevity. In short, PQQ activates dual oxidase. The nematode bli-3 gene corresponds to mammalian DUOX1 gene and DUOX2 gene.

Thus, the nematode variants can be used to determine how PQQ works. In the bli-3 variants, the nsy-1 variants, the pmk-3 variants, and the skn-1 gene variants encoding Nrf2 homologs, the life-extending effect was strongly suppressed, demonstrating that the gene group is essential for life extension. bli-3(e767) and bli-3(im10) are variants with reduced activity of dual oxidase. OB265 bli-3(e767); imEx144[bli-3genomic clone] is a line that restored the activity by the transfection of the bli-3 variant (e767) with the dual oxidase gene. These lines used were lines reported by Moribe et al. in PLOS GENETIC DOI: 10.1371/journal.pgen.1002957. Also, the nsy-1(ky400) and pmk-3 (ok169) variants are lines with reduced activity of ASK-1/MAPKKK, p38/MAPK.

As seen from these results, PQQ activates dual oxidase encoded by upstream bli-3. Then, ROS produced from the activated dual oxidase activates SKN-1/NRF-2 through the activation of the p38 MAPK cascade. It is evident that the dual oxidase activated by PQQ consequently enhances host defense response and contributes to life extension. It is generally recognized that reactive oxygen species (ROS) works to shorten life. Therefore, antioxidants are considered to be effective for the antiaging of living bodies. However, surprisingly, PQQ extends life by enhancing the functions of reactive oxygen species-producing enzymes, not serving as an antioxidant.

INDUSTRIAL APPLICABILITY

The life-extending agent and the dual oxidase activator of the present invention have industrial applicability for purposes such as foods, feed, and pharmaceutical products.

The invention claimed is:

1. A method, of extending life of a cell, the method comprising:
   administering an agent to a subject, which is a human or an animal,
   wherein the agent comprises a compound of formula (3) or a salt thereof:

(3)

where each R independently represents a hydrogen atom or a $C_1$-$C_{10}$ alkyl or allyl optionally substituted by O, N, S, or P.

2. A method for activating a dual oxidase, the method comprising:
   contacting the dual oxidase with a dual oxidase activator, wherein the dual oxidase activator comprises a compound of formula (3) or a salt thereof:

(3)

where each R independently represents a hydrogen atom or a $C_1$-$C_{10}$ alkyl or allyl optionally substituted by O, N, S, or P.

3. The method according to claim 1, wherein the subject is an adult human having a body weight of 60 kg and an amount administered to the subject is 0.25 to 1000 mg per day.

4. The method according to claim 1, wherein the agent comprises a pyrroloquinoline quinone sodium salt.

5. The method according to claim 4, wherein the pyrroloquinoline quinone sodium salt comprises a crystal having peaks at 2θ of 9.1±0.2°, 10.3±0.2°, 13.8±0.2°, and 24.0±0.2° by Cu-Kα radiation measurement in powder X-ray diffraction.

6. The method according to claim 2, wherein the dual oxidase is NADPH oxidase.

7. The method according to claim 2, wherein the dual oxidase activator comprises a pyrroloquinoline quinone sodium salt.

8. The method according to claim 7, wherein the pyrroloquinoline quinone sodium salt comprises a crystal having peaks at 2θ of 9.1±0.2°, 10.3±0.2°, 13.8±0.2°, and 24.0±0.2° by Cu-Kα radiation measurement in powder X-ray diffraction.

* * * * *